United States Patent [19]
Halloran et al.

[11] Patent Number: 5,225,190
[45] Date of Patent: * Jul. 6, 1993

[54] ORGANOSILICON HAIR CARE PRODUCTS

[75] Inventors: Daniel J. Halloran; Judith M. Vincent, both of Midland, Mich.

[73] Assignee: Dow Corning Corporation, Midland, Mich.

[*] Notice: The portion of the term of this patent subsequent to Jul. 6, 2007 has been disclaimed.

[21] Appl. No.: 927,107

[22] Filed: Aug. 10, 1992

Related U.S. Application Data

[60] Continuation of Ser. No. 762,125, Sep. 19, 1991, abandoned, which is a division of Ser. No. 608,913, Nov. 5, 1990, Pat. No. 5,108,738, which is a continuation-in-part of Ser. No. 549,196, Jul. 6, 1990, Pat. No. 5,135,742.

[51] Int. Cl.$^5$ ................................. A61K 7/11
[52] U.S. Cl. ..................... 424/70; 106/287.11; 106/287.13; 106/287.15; 252/174.15; 424/47; 424/71; 424/78.02; 424/78.03; 424/DIG. 1; 424/DIG. 2

[58] Field of Search ................... 106/287.11, 287.12, 106/287.13, 287.14, 287.15, 287.16; 252/173, 174.15; 427/387; 424/70, 47, 71, 78.02, 78.03, DIG. 1, DIG. 2

[56] References Cited

U.S. PATENT DOCUMENTS 5,022,922 6/1991 Itagaki et al. .................. 106/287.11
5,135,742 8/1992 Halloran et al. ...................... 424/70

Primary Examiner—Michael Lusigan
Attorney, Agent, or Firm—James L. DeCesare

[57] ABSTRACT

A hair treating method for imparting curl retention to hair in which at least one film forming ingredient is applied to the hair. The improvement utilizes as the film forming ingredient an organosilicon compound which is a hydrocarbon solvent free water soluble pre-hydrolyzed organofunctional silane having silsesquioxane characteristic. Hair care and fixative compositions including the silane are also disclosed.

6 Claims, No Drawings

ORGANOSILICON HAIR CARE PRODUCTS

RELATED PATENT APPLICATIONS

This application is a continuation of our prior copending application U.S. Ser. No. 07/762,125, filed Sep. 19, 1991, now abandoned; which is a division of our prior copending application U.S. Ser. No. 07/608,913, filed Nov. 5, 1990, now U.S. Pat. No. 5,108,738, issued Apr. 28, 1992; which is a continuation-in-part of our prior copending original parent application U.S. Ser. No. 07/549,196, filed Jul. 6, 1990, now U.S. Pat. No. 5,135,742, issued Aug. 4, 1992. All of the prior applications are assigned to the same assignee as the present application.

BACKGROUND OF THE INVENTION

This invention relates to new hair care products including fixative compositions and to improved methods of treating hair and providing curl retention to hair in which there is employed as the film forming ingredient certain hydrocarbon solvent free water soluble prehyrolyzed organofunctional silanes.

The cosmetic and toiletry industry has produced a wide range of grooming aids for use by men and women. Among the myriad of such products are shampoos to clean the hair and scalp, hair rinses, conditioners, dressings, sprays, wave sets, coloring and bleaching preparations, permanent waves, and hair strengthening compositions. Cleanliness of hair and scalp are important personal grooming criteria. Extensively soiled hair takes on a lackluster appearance and becomes oily and gritty to the touch. The shampoos must foam quickly and copiously, and rinse out thoroughly leaving the hair with a fresh clean scent, soft, shiny, lustrous, full bodied, and in a manageable state. While most shampoos are clear liquids and opaque lotions, they are available as clear gels, cream pastes, and aerosols. Shampoos contain one or more cleaning agents such as anionic, nonionic, amphoteric or ampholytic and cationic surfactants; and various additives including viscosity control agents, opacifiers, conditioners, preservatives, and fragrances. Wet hair is often tangled and difficult to comb following shampooing, and for this reason it is common to apply rinses and conditioners in order to enhance ease of combing, detangling, body, shine, texture, prevention of static buildup and manageability. Creme rinses and combination creme rinse conditioners also generally improve the finish of hair.

Fixatives are designed to provide a temporary setting effect or curl to the hair, and while the most common fixative is a hair spray which is designed to be applied to the hair after the hair has been blow dried, several specialty type fixatives can be applied either after the hair is towel dried or to dry hair, in order to provide more body and volume to the hair, and to aid in styling, modeling, and sculpting of the hair into unique new looks. This is followed by application of a hair spray in the form of an aerosol or pump spray to maintain the shape and style of the hair and provide gloss and sheen to the hair, in addition to a well groomed and natural appearance. Such specialty type fixatures are marketed under various names including styling gels, styling cremes, styling mousses, styling foams, styling sprays, styling spritz, styling mists, styling glazes, styling fixes; sculpting lotions, sculpting gels, sculpting glazes, sculpting sprays; glossing gels, glossing spritz; shaping gels; forming mousses; modeling spritz; finishing spritz; fixing gels; and setting lotions.

Whether the fixative is the more common hair spray or a specialty type fixative, it will typically include a film forming additive as the hair holding agent. The film forming additive should provide hair holding properties and curl retention, little flaking or powder on combing, rapid curing or drying on hair, nonstickiness, and be easily removable by shampooing. Film forming additives are delivered by a solvent which is usually an alcohol such as ethanol or a mixture of an alcohol and water. In the case of aerosol formulations such as hairsprays and mousses, a propellant such as isobutane, butane, propane or dimethyl ether is an added part of the delivery system.

Examples of currently used film forming agents are shellac, polyvinylpyrrolidone-ethyl methacrylate-methacrylic acid terpolymer, vinyl acetate-crotonic acid copolymer, vinyl acetate-crotonic acid-vinyl neodeconate terpolymer, poly(vinylpyrrolidone-ethyl-methacrylate methacrylic acid copolymer, vinyl methyl ether-maleic anhydride copolymer, octylacrylamide-acrylate-butylaminoethyl-methacrylate copolymer, and poly(vinylpyrrolidone-dimethylaminoethyl-methacrylate) copolymer and derivatives. These particular polymers are most suitable for alcohol based formulations such as hair sprays and pumps, and are sometimes used in water-based hair fixative products.

Such resins contain carboxyl groups which must be neutralized to some degree to provide compatibility with water to facilitate removal by shampooing and to increase the flexibility of the film. However, the greater the extent of neutralization, the less resistant the film is to high humidity. Therefore, although these resins can be rendered water soluble by neutralization, water-based fixative systems are not practical because of poor hold.

Polyvinylpyrrolidone and certain quaternary ammonium compounds such as Polyquaternium-11 which is an adopted name of the Cosmetic, Toiletry, and Fragrance Association are film forming additives used in completely water based fixative systems such as gels and mousses. However, these water soluble resins form films which are not resistant to high humidity. In fact, these polymers tend to be hygroscopic to the extent that exposure to high humidity actually softens and plasticizes the films through water absorption. Thus, a need exists for a fixative resin which is (i) completely water soluble without neutralization and provides high humidity resistance when applied from aqueous solutions, (ii) compatible with hydrocarbon propellants, and (iii) can be used in all the possible solvent systems for this application.

In accordance with the present invention, a new hair fixative formulation is provided which includes an organosilicon film forming material. Specifically, the organosilicon film forming material is a hydrocarbon solvent free water soluble organofunctional silane hydrolyzate. It is not new in the art to employ organosilicon compounds in hair fixative compositions. Nor is it new in the art to use silane type materials in hair fixatives. For example, organosilanes are disclosed in U.S. Pat. No. 2,782,790, issued Feb. 26, 1957; U.S. Pat. No. 4,344,763, issued Aug. 17, 1982; and in European Patent Application 85104416.4, published Oct. 30, 1985, under Publication No. 0 159 628 A2. While these references disclose various hair treating, hair setting, and hair waving methods which employ silanes, none of the prior art teaches the use of the particular water soluble pre-hydrolyzed organofunctional silane having silsesquioxane characteristic as disclosed herein.

In contrast to the organic film forming additives, the compositions of the present invention provide high humidity resistance from water, as well as ethanol-water solubility without neutralization. The polar functionility and the dispersability of the organosilicon materials permits the formation of solutions, emulsions, micro-emulsions, or suspensions in water. The silane hydrolyzates can also be delivered as aerosol solvents, or in volatile silicones, mineral oil, or other non-volatile hydrocarbons. This range of solubility is made possible by the chain flexibility of the molecule and by incorporating varying levels of organofunctionality. Other advantages include nonirritability, excellent shampoo removability, good sheen, low buildup, lack of tackiness, and reduced flaking.

SUMMARY OF THE INVENTION

This invention is directed to a hair treating method in which at least one film forming ingredient is applied to the hair. The improvement utilizes as the film forming ingredient an organosilicon compound. The preferred organosilicon compound is a hydrocarbon solvent free water soluble pre-hydrolyzed organofunctional silane having silsesquioxane characteristic.

This invention is also directed to a hair treating method for imparting curl retention to hair in which a film is formed on the hair, and the film is a hydrocarbon solvent free water soluble pre-hydrolyzed organofunctional silane having silsesquioxane characteristic.

The invention is further directed to hair care compositions which include the hydrocarbon solvent free water soluble pre-hydrolyzed organofunctional silane having silsesquioxane characteristic.

These and other features, objects, and advantages, of the present invention will become more apparent when considered in light of the following detailed description thereof.

DETAILED DESCRIPTION OF THE INVENTION

As noted above, the present invention relates to hair care products including fixatives products which utilize as the film forming ingredient a hydrocarbon solvent free water soluble pre-hydrolyzed organofunctional silane having silsesquioxane characteristic. Such silanes have been found to exhibit improved curl retention in comparison to conventional organic systems and provide the advantages of water compatibility, nonirritability, excellent aesthetics on hair, good wet and dry combing, excellent shampoo removability, good sheen, improved hold, low buildup, nontacky, and reduced flaking. The water soluble hydrolyzed silanes of the present invention also offer the added benefit that a plasticizer is not required although plasticizers may be included in the fixative composition if desired. Typical organic fixative systems include GANTREZ ® resins which are polymers consisting of the partial ethyl ether of the polycarboxylic resin formed from vinyl methyl ester and maleic anhydride. One of the GANTREZ ® resins is GANTREZ ® ES 225, a product and trademark of the GAF Corporation, Wayne N.J. This resin has been the film forming ingredient in such products as WHITE RAIN ® and FINAL NET ®. Such resins are typically employed as an ethanol based pump spray.

Several commercial hair fixative formulations are water based and include deep conditioners, styling gels, and mousses. While not primarily a hair fixative, the deep conditioners may contain a water soluble resin for imparting some degree of set retention. One organic film forming ingredient used in such water based organic systems is the GAFQUAT ® resin. Such resins are also products of the GAF Corporation, Wayne, N.J., and GAFQUAT ® is a trademark of that company. Exemplary of commercial resins are GAFQUAT ® 734 and GAFQUAT ® 755, known under the designation Polyquaternium-11 which is an adopted name of the Cosmetic, Toiletry, and Fragrance Association. While organosilicon compounds are not known to be water soluble, the hydrocarbon solvent free hydrolyzed silanes of the present invention are soluble in water based systems and hence possess utility in such systems in place of the organic GAFQUAT ® resin currently employed in the art.

The hydrocarbon solvent free water soluble pre-hydrolyzed organofunctional silanes of the present invention having silsesquioxane characteristic also have application in aqueous-alcohol based hair fixative systems. Aqueous ethanol is employed in some commercial spray-on pump and aerosol type products and mousses. The function of the alcohol in such system is to promote faster drying of the formulation relative to the water based type system. The silanes of the present invention may be used in anhydrous alcohol systems whether the system is designed for aerosol delivery or delivery by means of a pump spray device.

In the hair treating method in accordance with the present invention, the film forming ingredient is an organosilicon compound having in the molecule at least one moiety of the formula

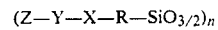

$$(Z-Y-X-R-SiO_{3/2})_n$$

wherein

X is a radical selected from the group consisting of amino, ammonium, quaternary amino, carbonyl, sulfonyl, and amido, or a sulfur or oxygen atom;

Y is an oxygen atom, a radical selected from the group consisting of alkylene, arylene, alkylarylene, alkyleneoxy, aryleneoxy, alkylaryleneoxy, carbonyl, and phosphoryl, or a covalent bond;

Z is hydrogen, or a radical selected from the group consisting of alkyl, alkenyl, aryl, amino, amido, ammonium, hydroxy, carboxy, vinyl, vinylbenzene, epoxy, vinylbenzylamino, alkylacrylo, polyalkyleneoxy, metal hydroxyl, alkylcarbonyl, arylcarbonyl, morphilino, and oxazolino;

R is a radical selected from the group consisting of alkylene, arylene, alkylarylene, and alkenylene, or an oxygenated, aminated, amidated, or thiolated, substitution thereof; and n is an integer from one to ten thousand.

These pre-hydrolyzed organofunctional silanes having silsesquioxane characteristic are applied to the hair as a mixture including a solvent. The organosilicon compound is present in the mixture at a level from about 0.1 to about fifty percent by weight based on the weight of the mixture. Preferably, the organosilicon compound is present in the mixture at a level from about three to about thirty percent by weight based on the weight of the mixture. The solvent is preferably water, but a hydrocarbon, alcohol, or blend of alcohol and water may be used. Where the solvent is a hydrocarbon, it is preferred to employ materials such as dimethylether, liquefied petroleum gas, propane, and isobutane. In the event the solvent is an alcohol, some appropriate materials are methanol, ethanol, and isopropanol.

With regard to the compounds expressed in the above formula, the alkyl, alkenyl, and alkylene radicals, preferably contain from one to twenty carbon atoms. It should also be noted that where the composition bears a positive charge, the anion may be a weak acid carboxylate, sulfate, nitrate, benzoate, halide, or other anion. Where the compound is aminofunctional, it may be protonated with a protonic acid or neutralized without protonation with a Lewis acid. The compounds may be linear, cyclic, or of ladder structure. Such compounds can also be dimerized, trimerized, or partially dimerized or trimerized through the X, Y, and Z groups. These compounds may be employed with fillers if desired. The organosilicon compounds in accordance with the present invention further may be soluble materials; micellar; capable of forming submicron aggregates such as vesicles or microemulsions; or liquid crystalline in structure depending on the solvent system employed. Such compounds may be homopolymers, copolymers, terpolymers, or blends including other silicone or organic compositions.

One preferred compound in accordance with the present invention is a pre-hydrolyzed organofunctional silane having silsesquioxane characteristic and containing in the molecule at least one moiety of the formula

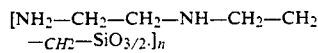

The interger n in the above formula can vary between one and about twenty. This pre-hydrolyzed silane can be applied to the hair as a mixture including a solvent, and if desired, at least one additional ingredient such as propellants, conditioners, surfactants, plasticizers, thickeners, preservatives, and fragrances.

In accordance with a first embodiment, the silanes of the present invention were dissolved in ethanol and tested for curl retention. These formulations were compared to a commercial aerosol product containing about four to five percent by weight of the film forming resin ingredient RESYN ® 28-2930 manufactured by National Starch and Chemical, Bridgewater, N.J. The hydrolyzed silanes provided curl retentions beyond the curl retention obtained with the commercial product, and at levels ranging from about one to five percent by weight of the silane. In experiments involving multiple hair tresses, the silanes provided more consistent results than the corresponding commercial product. Similar results were achieved in tests comparing the hydrolyzed silane film formers of the present invention with another commercial product FINAL NET ®. The results of these tests and their procedures are set forth below.

The following examples are set forth in order to illustrate in more detail the concepts embodied by one embodiment of the present invention.

EXAMPLE I

Into a three necked round bottom flask equipped with a stirrer and thermometer was placed 66.2 grams of ethylenediamino-propyltrimethoxy silane of the formula $NH_2CH_2CH_2NHCH_2CH_2CH_2Si(OCH_3)_3$. To the flask was added thirty grams of a fifty-fifty blend of n-octanol and n-decanol. The silane and the alcohol blend was mixed thoroughly. To the mixture was slowly added 3.8 grams of deionized water, and the contents of the flask was allowed to mix for about one hour. The flask was heated to one hundred-sixty degrees Centigrade while stripping methanol. After the flask was cooled, the product was recovered and identified to be a pre-hydrolyzed organofunctional silane having silsesquioxane characteristic, and having in the molecule at least one moiety of the formula

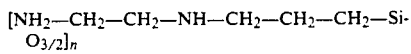

EXAMPLE II

The hydrolyzed silane of EXAMPLE I was formulated into a hair fixative composition by mixing the hydrolyzed silane with ethanol in order to provide various fixative formulations containing one, two, three, and five percent by weight of the silane. These hydrocarbon solvent containing silane hair fixative formulations were evaluated for curl retention and compared to commercial hair fixative products in accordance with the procedures set forth below. The results of such evaluations and comparisons are provided in the accompanying Tables.

EXAMPLE III

Hair fixative formulations were evaluated by employing six inch hair tresses of approximately two grams of untreated human hair. Each tress was made by gluing the top part of the hair to a 2"×2" plastic tab. After drying on the tab, the hair was trimmed to six inches. Each tress was then cleaned with an anionic/amphoteric shampoo of the following formulation:

| | |
|---|---|
| Distilled Water | 61.45% |
| Methylchlorisothiazolinone and methylisorhiazolinone | 0.05% |
| Ammonium Lauryl Sulfate | 35.00% |
| Lauramide DEA | 3.00% |
| Sulfuric Acid | q.s. |
| Ammonium Chloride | 0.50% |

The tress was first rinsed for 15 minutes under 40 degree Centigrade tap water and 0.5 cc of the above shampoo was applied. Shampooing for 30 seconds was followed by a 30 second rinse. The tresses were then set on plastic rollers approximately ½ in. in diameter and allowed to dry overnight. Hair fixative formulations were applied to the hair either by dripping on 0.5 g or by spraying on 0.3 g. If the drip application was used, the hair was combed three times and reset on a roller. If the resin solution was delivered from a pump, the hair was not reset. The solution was allowed to cure on the hair for a period of one to two hours for ethanol-based and overnight for water-based formulations. The dried tresses were hung in a constant humidity chamber at 90 percent relative humidity and initial readings were taken as well as additional readings at predetermined intervals. If the tress was reset the roller was removed prior to exposure.

Curl retention was calculated as the extended length minus the length at the end of the predetermined interval divided by the extended length minus the initial length. Tables I and II represent curl retention after 24 hours of exposure and evidence excellent performance of the silane hydrolyzate at low add-on levels in comparison to the organic control.

TABLE I

| Percent Silane in Ethanol | Curl Retention (Percent) |
| --- | --- |
| 1.0 | 96 |
| 2.0 | 96 |
| 3.0 | 96 |
| 5.0 | 94 |

TABLE II

| Percent GANTREZ ® in Ethanol | |
| --- | --- |
| 1.0 | 0 |
| 2.0 | 0 |
| 3.0 | 73 |

EXAMPLE IV

Into a three neck round bottom flask equipped with a stirrer, thermometer and nitrogen inlet was placed 60 grams of ethylenediaminopropyltrimethoxy silane. To the flask was added 425 grams of 200 proof ethanol and 15 grams de-ionized water while stirring. The mixture was refluxed under nitrogen for more than one hour. After cooling, the solution was poured out into evaporating equipment and the solvent was evaporated off at room temperature. The solid was then redissolved in 150 grams 200 proof ethanol in a flask under nitrogen while heating.

EXAMPLE V

The hydrolyzed silane of Example IV was formulated into a hair fixative composition by mixing the hydrolyzed silane with ethanol in order to provide various hydrocarbon solvent containing fixative formulations containing three, five and ten percent by weight of the silane.

EXAMPLE VI

The hair fixative formulations of Example V were evaluated according to the procedure described in Example III. The organic resin GANTREZ ® ES225 was used as the control comparison. The results of these evaluations are given below.

TABLE III

| | Curl Retention (Percent) |
| --- | --- |
| Percent Silane in Ethanol | |
| 3.0 | 86 |
| 5.0 | 98 |
| 10.0 | 98 |
| Percent Gantrez ® in Ethanol | |
| 3.0 | 73 |
| 5.0 | 93 |
| 10.0 | 98 |

EXAMPLE VII

Part A: Into a four ounce bottle was added forty grams 200 proof ethanol and four grams methyltrimethoxysilane of the formula $CH_3Si(OCH_3)_3$. Part B: Into another four ounce bottle was added 1.5 grams de-ionized water and 0.6 grams ethylenediaminopropyltrimethoxysilane. After mixing both parts Part A was added to Part B.

EXAMPLE VIII

Part A: Into a four ounce bottle was added forty grams 200 proof ethanol and four grams propyltrimethoxysilane of the formula $CH_3CH_2CH_2Si(OCH_3)_3$.

Part B: Into another four ounce bottle was added 1.5 grams de-ionized water and 0.6 grams ethylenediaminopropyltrimethoxysilane. After mixing Part A was added to Part B.

EXAMPLE IX

The materials prepared in Examples VII and VIII were evaluated as hydrocarbon solvent containing hair fixatives without further dilution or modification. The procedures used were those set forth in Example III and the results are noted below.

TABLE IV

| Solution | Percent Silane in Ethanol | Curl Retention (Percent) |
| --- | --- | --- |
| Example VII | 8.7 | 98 |
| Example VIII | 8.7 | 99 |

EXAMPLE X

Into a four ounce glass bottle was added 36 grams of deionized water. While stirring, four grams of ethylenediaminopropyltrimethoxysilane was slowly added. Stirring was continued to insure complete mixing. At least sixteen hours was allowed to elapse prior to evaluation to ensure complete hydrolysis.

EXAMPLE XI

Example X was repeated using the silane 3-(trimethoxysilyl)-propyldimethyloctadecyl ammonium chloride of the formula $Cl-(MeO)_3SiCH_2CH_2CH_2(CH_3)_2N^+C_{18}H_{37}$.

EXAMPLE XII

Example X was repeated using sodium-3-trihydroxysilyl-propylmethyl phosphonate of the formula $(HO^-)_3SiCH_2CH_2CH_2OP=O(CH_3)O^-Na^+$.

EXAMPLE XIII

The materials prepared in Examples X, XI, and XII, were evaluated as water based fixatives without further dilution or modification. The procedures used were those employed in Example III and results are set forth in Table V including comparisons to PVP K-30 (polyvinylpyrrolidone) and GAFQUAT ® 755N.

TABLE V

| Solution | | Curl Retention (Percent) |
| --- | --- | --- |
| | Percent Silane in Water | |
| Example XII | 10 | 93 |
| Example XIII | 10 | 94 |
| Example XIV | 10 | 94 |
| | Percent Resin in Water | |
| PVP K-30 | 10 | 0 |
| GAFQUAT ® 755N | 10 | 0 |

PVP K-30 is a polyvinylpryyolidone polymer with an average molecular weight of 40,000. GARQUAT ® 755N is a quaternized copolymer of vinylpyrrolidone and dimethylaminoethyl methacrylate with an average molecular weight of 1,000,000 and the CTFA designation of Polyguaternium-23.

Materials preferred in accordance with the present invention are compounds produced from the following silanes as starting materials:

$(MeO)_3SiCH_2CH_2CH_2NHCH_2CH_2NH_2$ $(MeO)_3SiCH_2CH_2CH_2NH_2$ $Cl^-(MeO)_3SiCH_2CH_2CH_2(Me)_2N^{\oplus}C_{18}H_{37}$ $(MeO)_3SiCH_2CH_2CH_2OCH_2CH(OH)CH_2NHCH_2CH_2NH_2$ $(MeO)_3SiCH_2CH_2CH_2NHCH_2CH_2NHCH_2\phi CH=CH_2HCl$

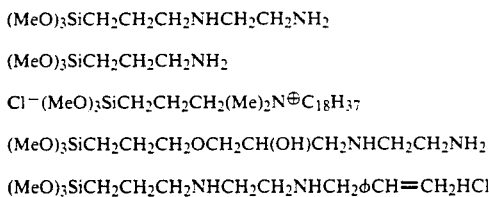

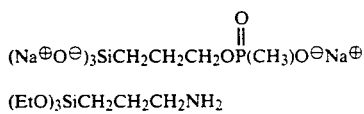

$(EtO)_3SiCH_2CH_2CH_2NH_2$ and

It has been found that the above silanes can be formed into hydrocarbon solvent free water soluble pre-hydrolyzed organofunctional silanes having silsesquioxane characteristic. This provides a significant advantage in that it is possible to formulate these materials into aqueous hair care solutions which comply with the various federal and state volatile organic compound (VOC) regulations relating to the liberation of certain prohibited substances. These organosilicon resin flake materials may be reconstituted and dissolved in water to form aqueous solutions which is highly unexpected and unique since organosilicon materials are not known to be water soluble.

This is accomplished by isolating the pre-hydrolyzed silane as a solid by removing any solvent completely, flaking the isolated hydrocarbon solvent free solid, and redissolving the flaked solid in water. The result is an aqueous solution having dissolved therein the organosilicon material. The components of the solutions of the present invention have been found to be homogeneously mixed and the components of these solutions are subdivided to such an extent that there is no appearance of light scattering visible to the naked eye when a one inch diameter bottle of the mixture is viewed in sunlight. The aqueous solutions containing these flaked organosilicon resin materials are homogeneous, clear, substantially transparent, and are stable for extended periods of time without the essential components becoming destabilized. The organosilicon resin material readily dissolves in water. While a solution instead of a microemulsion is formed, the organosilicon resin material is capable of being delivered in emulsion or microemulsion form in appropriate situations.

The following examples further amplify this alternate embodiment of the present invention and illustrate methods of preparing these novel VOC compliant hair treating additives.

EXAMPLE XIV

Thirty parts of ethylenediaminopropyltrimethoxy silane of the formula $NH_2CH_2CH_2NHCH_2CH_2CH_2Si(OCH_3)_3$ were added to seventy parts deionized water with stirring. The solution was aged for four months in a covered glass bottle. A portion of the solution was isolated as a solid under nitrogen and redissolved in deionized water at a level of ten percent by weight. The resulting solution was employed as a hair fixative and evaluated as described in Example XX.

EXAMPLE XV

Thirty parts of ethylenediaminopropyltrimethoxy silane of the formula $NH_2CH_2CH_2NHCH_2CH_2CH_2Si(OCH_3)_3$ were added to seventy parts deionized water with stirring. The solution was aged for three days in a covered glass bottle. A portion of the solution was isolated as a solid under nitrogen and redissolved in deionized water at a level of ten percent by weight. The resulting solution was employed as a hair fixative and evaluated as described in Example XX.

EXAMPLE XVI

Thirty parts of ethylenediaminopropyltrimethoxy silane of the formula $NH_2CH_2CH_2NHCH_2CH_2CH_2Si(OCH_3)_3$ were added to seventy parts deionized water with stirring. Hydrochloric acid was added to neutralize the amine producing a pH of approximately 7. The solution was aged for three days in a covered glass bottle. A portion of the solution was isolated as a solid under nitrogen and redissolved in deionized water at a level of ten percent by weight. The resulting solution was employed as a hair fixative and evaluated as described in Example XX.

EXAMPLE XVII

Thirty parts of ethylenediaminopropyltrimethoxy silane of the formula $NH_2CH_2CH_2NHCH_2CH_2CH_2Si(OCH_3)_3$ were added to seventy parts deionized water with stirring. In a separate container, 66.7 parts PVP K-60 was added to 33.3 parts deionized water. The aminosilane solution was combined with the PVP. The sample was aged for three days in a covered glass bottle. A portion of the solution was isolated as a solid under nitrogen and redissolved in deionized water at a level of ten percent by weight. The resulting solution was employed as a hair fixative and evaluated as described in Example XX. PVP K-60 is polyvinylpyrrolidone with an average molecular weight of 160,000. It is manufactured by the GAF Chemical Corporation of Wayne, N.J. and is supplied as a 45% solids aqueous solution.

EXAMPLE XVIII

Thirty parts of aminopropyltrimethoxy silane of the formula $NH_2CH_2CH_2CH_2Si(OCH_3)_3$ were added to seventy parts deionized water with stirring. The solution was aged for three days in a covered glass bottle. A portion of the solution was isolated as a solid under nitrogen and redissolved in deionized water at a level of ten percent by weight. The resulting solution was employed as a hair fixative and evaluated as described in Example XX.

EXAMPLE XIX

Eighty-one parts of 3-trimethoxysilyl)propyldimethyloctadecyl ammonium chloride of the formula $(CH_3O)_3SiCH_2CH_2CH_2(CH_3)_2N^+C_{18}H_{37}Cl^-$ as a 72% solids solution in methanol were added to nineteen parts deionized water. The solution was aged for three months in an covered glass bottle. A portion of the solution was isolated as a solid under nitrogen. The resulting solid was not soluble in water. However, a fine dispersion of the solid was made in water at a level of ten percent by weight by heating for a period of one hour at a temperature of sixty degrees Centigrade while mixing with shear. The resulting dispersion was employed as a hair fixative and evaluated as described in Example XX.

EXAMPLE XX

The hair fixative formulations were evaluated in accordance with Example III except that citric acid was used instead of sulfuric acid, and the formulations were applied with an eyedropper. The fixative formulations of Examples XIV—XIX were evaluated as described and curl retention results are set forth in Table VI. Control comparisons were provided by testing ten weight percent solutions of several water-soluble organic resins.

TABLE VI

| Fixative Solution | Curl Retention (Percent) | | | | |
|---|---|---|---|---|---|
| | 1 hr. | 2 hr. | 4 hr. | 16 hr. | 24 hr. |
| EXAMPLE XIV | — | — | — | — | 83 |
| EXAMPLE XV | 100 | 98 | 96 | 83 | 81 |
| EXAMPLE XVI | 96 | 96 | 92 | 85 | 0 |
| EXAMPLE XVII | 100 | 96 | 95 | 88 | 82 |
| EXAMPLE XVIII | 98 | 97 | 97 | 90 | 0 |
| EXAMPLE XIX | 95 | 95 | 95 | 95 | 92 |
| Comparitive Examples 10% Solids in Water* | | | | | |
| PVP K-30 | 98 | 90 | 60 | 0 | |
| PVP K-60 | 98 | 90 | 35 | 0 | |
| PVP K-90 | 97 | 94 | 76 | 0 | |
| GAFQUAT ® 845 | 96 | 93 | 90 | 45 | 0 |
| GAFQUAT ® 937 | 97 | 95 | 93 | 38 | 0 |

*PVP K-30: polyvinylpyrrolidone average molecular weight 40,000
*PVP K-60: polyvinylpyrrolidone average molecular weight 160,000
*PVP K-90: polyvinylpyrrolidone average molecular weight 360,000
GAFQUAT ® 845 and 937 are copolymers of vinylpyrrolidone and dimethylaminoethylmethacrylate monomers and manufactured by the GAF Chemicals Corporation, Wayne, New Jersey.

The compositions of this invention may contain emulsifying agents such as anionic, amphoteric, nonionic, cationic, and zwitterionic surfactants. Suitable anionic detergents include sulfonated and sulfated alkyl, aralkyl and alkaryl anionic detergents; alkyl succinates; alkyl sulfosuccinates and N-alkyl sarcosinates. Surfactants generally classified as amphoteric or ampholytic detergents include cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents include the quaternary cycloimidates, betaines, and sultaines disclosed in U.S. Pat. No. 3,964,500.

The compositions may contain a nonionic surfactant such as fatty acid alkanolamide and amine oxide surfactants. Appropriate cationic surfactants include quaternary ammonium salts of primary, secondary and tertiary fatty amines. Zwitterionic surfactants which may be employed are quaternary ammonium, phosphonium, and sulfonium compounds containing aliphatic substituents one of which is carboxy, phosphate, phosphonate, sulfate, or sulfonate functional.

Other adjuvants may be added such as plasticizers, thickeners, perfumes, colorants, electrolytes, pH control ingredients, antimicrobials, antioxidants, ultraviolet light absorbers and medicaments. When the fixative is in the form of a gel or lotion, it is sometimes preferred to employ a thickener in the compositions to facilitate the hand application of the composition to the hair. Thickeners are preferably used in sufficient quantities to provide a convenient viscosity. For example, viscosities within the range of 400 to 6000 cps are preferred for lotions. Higher viscosities are preferred for gels whereas lower viscosities are preferred for sprays.

Suitable thickeners, include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as NaCl, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the present invention. Electrolytes including sodium chloride and ammonium chloride provide thickening particularly in aqueous systems and may also be employed.

Representative plasticizers that may be employed include polyproplylene glycol, glycerine, and polysiloxanes. Siloxane polymers such as polydimethylsiloxane, cyclic polydimethylsiloxane, phenylpolydimethylsiloxane, and polydimethylsiloxane with methylene and or propylene oxide side chains, are particularly preferred.

The perfumes used must be cosmetically acceptable perfumes. Colorants can be used to confer a color to the composition. Although not required, it is preferred to employ an acid or base to adjust the pH within the range of 5 to 9 or more preferably within the range of 6 to 8. Any water soluble acid such as a carboxylic acid or a mineral acid is suitable. For example, acids which may be employed include mineral acids such as hydrochloric, sulfuric, and phosphoric, monocarboxylic acids such as acetic acid, lactic acid, or propionic acid; and polycarboxylic acids such as succinic acid, adipic acid and citric acid. Where a base is required, organic amines such as 2-amino-2-methyl-1-propanol are appropriate.

For special purposes conditioners may be added such as any of the well-known organic cationic hair conditioning components. Some cationic conditioning components that may be used to provide hair grooming include quaternary nitrogen derivatives of cellulose ethers, homopolymers of dimethyldiallyl-ammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-α,ω-bis-(triethanolammonium) chloride, and copolymers of vinylpyrrolidone and acrylic acid esters with quaternary nitrogen functionality. These cationic organic polymers are described in U.S. Pat. No. 4,240,450 which is incorporated by reference. Other categories of organic conditioners which may also be employed are proteins, monomeric organic quaternarys and betaines. Silicone conditioning agents may be employed such as cyclomethicone, dimethicone, phenyldimethicone, dimethicone copolyol, amodimethicone, and trimethylsilylamodimethicone.

A preservative may be required and representative preservatives include about 0.1–0.2 weight percent of compounds such as formaldehyde, dimethyloldimethylhydantoin, 5-bromo-5-nitro-1,3-dioxane, methyl- and propyl para-hydroxybenzoates, and mixtures of such benzoates with sodium dehydroacetate, sorbic acid, and imidazolidinyl urea.

The compositions may also be formulated to include dyes, colorants, reducing agents, neutralizing agents, and preservatives, necessary for their application as permanent wave systems or hair dyes. The active formulation can be applied in several different forms including lotions, gels, mousses, aerosols, and pump sprays, and as conditioners and shampoos. The active ingredient includes a carrier, and suitable carrier fluids for hair care formulations are preferably water. However, such fluids as alcohols namely ethanol or isopropanol, hydrocarbons and halogenated hydrocarbons such as mineral spirits and trichloroethane, supercritical fluids such as supercritical carbon dioxide and nitrogen, cyclic siloxanes, and aerosol propellants may be used. In those instances where it is desired to incorporate the active in the form of either an emulsion or microemulsion, such emulsions may be prepared in accordance with either U.S. Pat. No. 4,501,619, issued Feb. 26, 1985, which is directed to emulsions, or U.S. Pat. No. 4,620,878, issued Nov. 4, 1986, relating to microemulsions, each of which is incorporated herein by reference.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether. Where the solvent system is alcohol free, mechanical and chemical drying agents may also be employed in spray and aerosol formulations.

It will be apparent from the foregoing that many other variations and modifications may be made in the compounds, compositions, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A method of making a prehydrolyzed silsesquioxane having the formula:

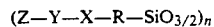

wherein

X is a radical selected from the group consisting of amino, ammonium, quaternary amino, carbonyl, sulfonyl, and amido, or an oxygen atom;

Y is an oxygen atom, a radical selected from the group consisting of alkylene, arylene, alkylarylene, aryleneoxy, alkylaryleneoxy, carbonyl, and phosphoryl, or a covalent bond;

Z is hydrogen or a radical selected from the group consisting of alkyl, alkenyl, aryl, amino, amido, ammonium, hydroxy, carboxy, vinyl, vinylbenzene, epoxy, vinylbenzylamino, alkylacrylo, metal hydroxyl, alkylcarbonyl, arylcarbonyl, morphilino, and oxazolino;

R is a radical selected from the group consisting of alkylene, arylene, alkylarylene, and alkenylene, or an oxygenated, aminated, amidated, or thiolated substitution thereof; and n is an integer having a value of from one to ten thousand, comprising (i) adding a silane to an alcohol in a vessel; (ii) mixing the silane and the alcohol; (iii) adding water to the silane and alcohol; (iv) mixing the silane, alcohol, and water; (v) isolating a solid silsesquioxane product by heating the vessel to evaporate the alcohol and water; (vi) cooling the vessel and removing the solid silsesquioxane product from the vessel; the silane being a compound selected from the group consisting of ethylenediaminopropyltrimethoxysilane; propyltrimethoxysilane; 3-(trimethoxsilyl)-propyldimethylammonium chloride; sodium-3-trihydroxysilylpropylmethyl phosphonate; and aminopropyltrimethoxysilane.

2. The method of claim 1 in which the alcohol is a compound selected from the group consisting of ethanol, isopropanol, n-octanol, and n-decanol.

3. The method of claim 1 in which the silsesquioxane has the formula $(NH_2CH_2CH_2NHCH_2CH_2CH_2SiO_{3/2})_n$.

4. A method of providing curl retention to hair comprising flaking the solid silsesquioxane produced by the method of claim 1; dissolving the flaked solid silsesquioxane in water to form a solution; and applying the solution to hair.

5. A method of providing curl retention to hair comprising flaking the solid silsesquioxane produced by the method of claim 1; dissolving the flaked solid silsesquioxane in an alcohol to form a solution; and applying the solution to hair.

6. A method according to claim 5 in which the alcohol is a compound selected from the group consisting of ethanol, isopropanol, n-octanol, and n-decanol.

* * * * *